United States Patent
Smolik

Patent Number: 6,061,839
Date of Patent: May 16, 2000

[54] UNDERSHORTS HAVING PROTECTIVE LINER

[76] Inventor: Robert A. Smolik, 670 W. 7th St., St. Paul, Minn. 55102

[21] Appl. No.: 09/318,097

[22] Filed: May 25, 1999

Related U.S. Application Data

[63] Continuation-in-part of application No. 09/251,320, Feb. 17, 1999.

[51] Int. Cl.[7] .................................................. A41B 9/00
[52] U.S. Cl. .................... 2/400; 2/403; 2/406; 604/385.1
[58] Field of Search ........................ 2/400–408; 604/358, 604/374, 378–384, 385.1, 386, 387, 389–394, 396–398, 401

[56] References Cited

U.S. PATENT DOCUMENTS

| | | |
|---|---|---|
| 2,821,196 | 1/1958 | Spiro . |
| 3,088,462 | 5/1963 | Muto . |
| 4,338,939 | 7/1982 | Daville . |
| 4,589,876 | 5/1986 | Van Tilburg ......................... 604/385.1 |
| 5,087,254 | 2/1992 | Davis et al. ............................ 604/386 |
| 5,210,882 | 5/1993 | Moretz et al. . |
| 5,290,270 | 3/1994 | Fisher . |
| 5,618,279 | 4/1997 | Pudlo ................................... 604/385.1 |
| 5,716,350 | 2/1998 | Ryan .................................... 604/385.1 |
| 5,772,650 | 6/1998 | Mizutani ................................. 604/387 |

*Primary Examiner*—Gloria M. Hale
*Attorney, Agent, or Firm*—James W. Miller

[57] ABSTRACT

A pair of undershorts is provided with a removable liner. The liner is generally rectangular in shape and includes a sidewardly extending flap intermediate two spaced first and second ends of the liner. Each end of the liner is attached adjacent the waistband of the undershorts with one end being attached to the front of the shorts and the other end being attached to the back of the shorts with the liner draping down to follow the curve of the undershorts and overlie the crotch of the undershorts. The flap extends out through one leg hole of the undershorts to wrap around a portion of the crotch and then passes back in through the other leg hole of the undershorts to be detachably secured to the liner. Alternatively, two sidewardly extending flaps could be used with each flap passing out through one leg hole and passing only partway over a portion of the crotch. The liner effectively catches or absorbs unintended urinary or fecal discharges to prevent the user's undershorts and/or outer garments from becoming stained or soiled.

20 Claims, 4 Drawing Sheets

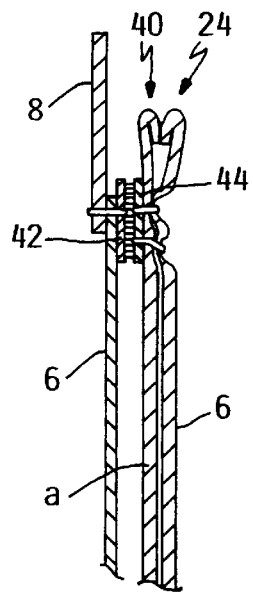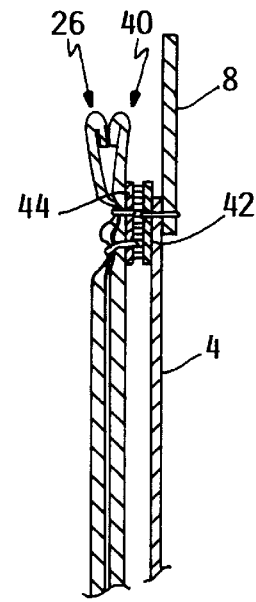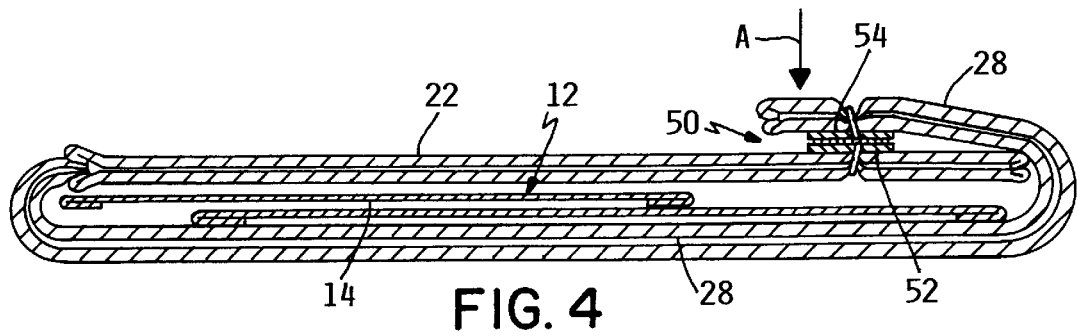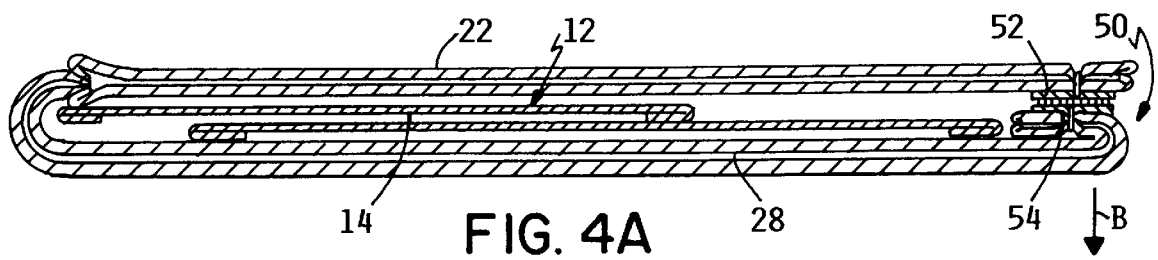

UNDERSHORTS HAVING PROTECTIVE LINER

CROSS REFERENCE TO RELATED APPLICATIONS

This application is a continuation-in-part of application Ser. No. 09/251,320, filed Feb. 17, 1999, pending.

TECHNICAL FIELD

This invention relates to undershorts or the like having a protective liner for preventing the undershorts, or the outer garments which cover the undershorts, from being soiled or stained by various types of bodily discharges. The liner is easily removable and replaceable.

BACKGROUND OF THE INVENTION

Undershorts of various types are known which are worn beneath an outer garment for protecting the outer garment from being soiled or stained by urinary or fecal discharge or residue. Men's undershorts come in two basic styles, a jockey style or a brief style. Both of these men's undershorts typically have a fly at the front for protrusion of the penis during urination. Women's undershorts or panties are similar in many respects, although the fly may be absent from women's undershorts.

There are numerous medical conditions in which unwanted urinary or fecal discharges can take place. For example, colitis is a condition in which diarrhea like fecal discharges often occur. Such discharges can quickly and severely soil the undershorts. If such undershorts are not quickly changed, the soiling will spread to the outer garments that cover the undershorts. Since a change of undershorts is not always possible, as when the wearer is away from home, the unintended soiling of the undershorts and the outer garments is a distinct and unfortunate possibility.

The soiling of one's undershorts and outer garments has various disadvantages. One is the embarrassment that results if the soiling becomes visible to others while the wearer is in public. Another is the need to frequently clean the undershorts and outer garments that have become stained. Often, the staining is so severe that cleaning cannot remove the stains, requiring that the soiled items be thrown away and replaced. This is obviously expensive and to be avoided if possible.

Various types of removable liners have been proposed for use inside undershorts to catch or absorb unintended urinary or fecal discharges before they soil or stain the undershorts. For example, U.S. Pat. No. 2,821,196 to Spiro and 3,088,462 to Muto show two examples of such liners.

However, known liners for undershorts have various difficulties. Often, they only cover small areas of the undershorts. Thus, if the unintended urinary or fecal discharge happens to reach an area of the undershorts not covered by the liners, soiling or staining will still occur. In addition, known liners are not directly attached to the crotch area of the undershorts. This leaves open the possibility that the bodily discharges can leak around the sides of the liners in the crotch area and again reach the undergarment to soil or stain it. Thus, there is a need for a more secure and extensive liner to better protect the undershorts, and hence the outer garments covering the undershorts, from staining or soiling.

SUMMARY OF THIS INVENTION

One aspect of this invention is to provide a liner that more completely and securely covers the inside of a pair of undershorts.

This aspect of the invention is provided by pair of undershorts having a liner and to the undershort/liner combination. This combination comprises a pair of undershorts which includes a front, a back, a waistband, two leg holes, and a crotch between the leg holes. A liner is attached to the undershorts and covers at least a portion of the front and a portion of the back of the undershorts. The liner has at least one sidewardly extending flap that is positioned to extend out through one leg hole and wrap around at least a portion of the crotch.

Another aspect of this invention relates to an undershort/liner combination which comprises a pair of undershorts which includes a front, a back, a waistband, two leg holes, and a crotch between the leg holes. A liner is attached to the undershorts and covers substantially the entire front and back of the undershorts. The liner has a first end attached to the undershorts at the front adjacent the waistband and a second end attached to the undershorts at the back adjacent the waistband. The liner extends between its first and second ends with a length and width which is sufficient to drape downwardly between the first and second ends of the liner to closely cover and overlie both the back, the front and the crotch of the undershorts.

BRIEF DESCRIPTION OF THE DRAWINGS

This invention will be described more completely in the following Detailed Description, when taken in conjunction with the following drawings, in which like referenced numerals refer to like elements throughout.

FIG. 2 is a partial cross-sectional view of the undershorts shown in FIG. 1 taken along lines 2—2 in FIG. 1, illustrating the attachment of one end of the liner to the waistband at the rear of the undershorts;

FIG. 3 is a partial cross-sectional view of the undershorts shown in FIG. 1 taken along lines 3—3 in FIG. 1, illustrating the attachment of one end of the liner to the waistband at the front of the undershorts;

FIG. 4 is a partial cross-sectional view of the undershorts shown in FIG. 1 taken along lines 4—4 in FIG. 1, illustrating a first embodiment for fastening the crotch wrapping portion of the liner to the liner after the crotch wrapping portion has been wrapped around the crotch of the undershorts;

FIG. 4A is a partial cross-sectional view of the undershorts shown in FIG. 1 taken along lines 4—4 in FIG. 1, illustrating a second embodiment for fastening the crotch wrapping portion of the liner to itself after the crotch wrapping portion has been wrapped around the crotch of the undershorts;

DETAILED DESCRIPTION

Figure 1:
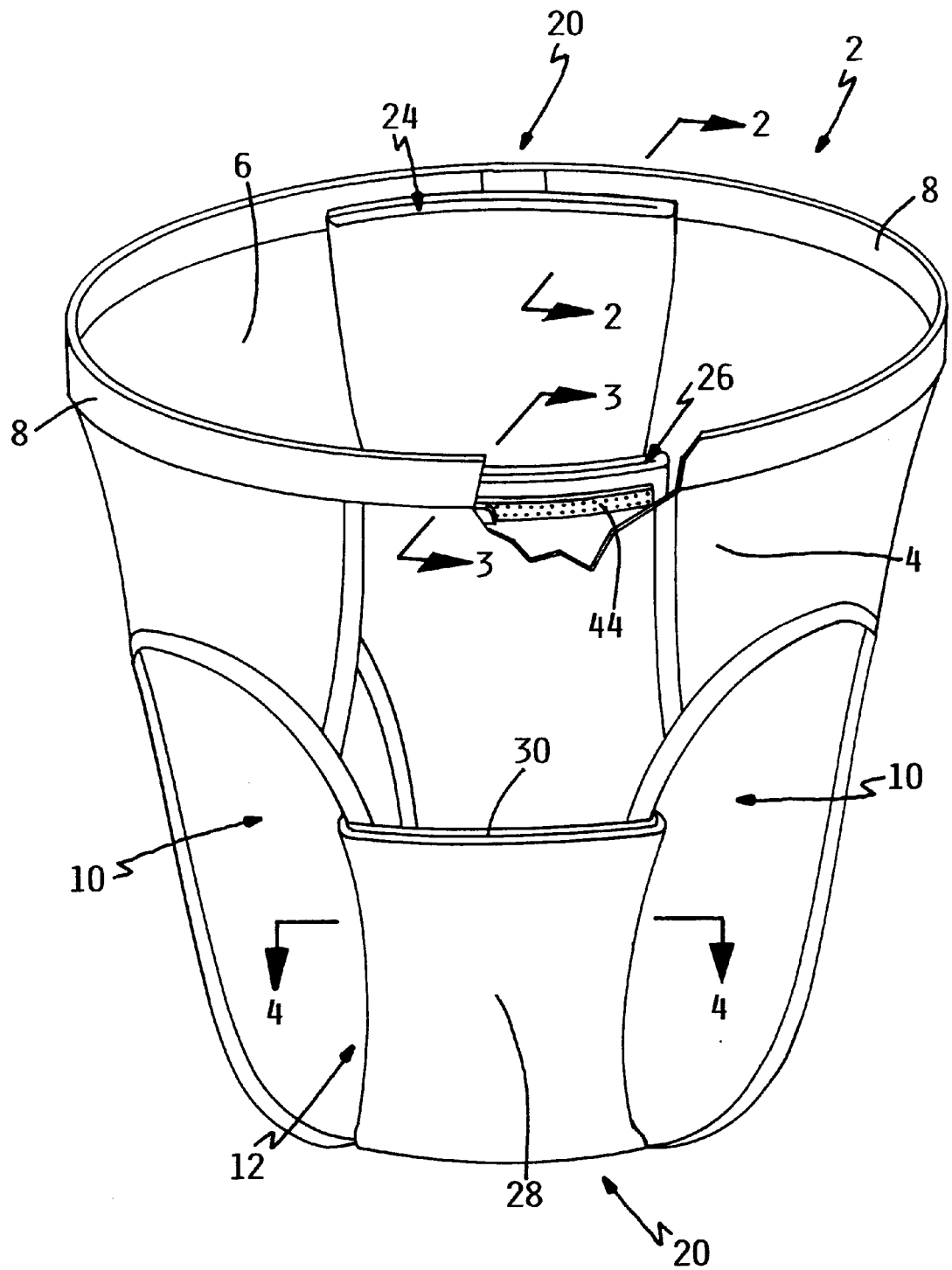
FIG. 1 is a perspective view of a pair of undershorts according to this invention having a protective, removable liner, a portion of the undershorts being broken away in the front at the waistband to better illustrate that end of the liner which would otherwise have been hidden in this view.

Referring first to FIG. 1, a typical pair of men's undershorts in the jockey style is shown as 2. Undershorts 2 include a front 4, a back 6, a waistband 8, and two leg holes 10 through which the legs (not shown) of the wearer protrude when undershorts 2 are being worn. Undershorts 2 also include a crotch 12 located between the two leg holes 10. A fly 14 is also on front 4 of undershorts 2 in a portion of crotch 12. Fly 14 includes an opening through which the penis can protrude during urination. However, fly 14 can be dispensed with in undershorts 2 intended for women.

Figure 5:
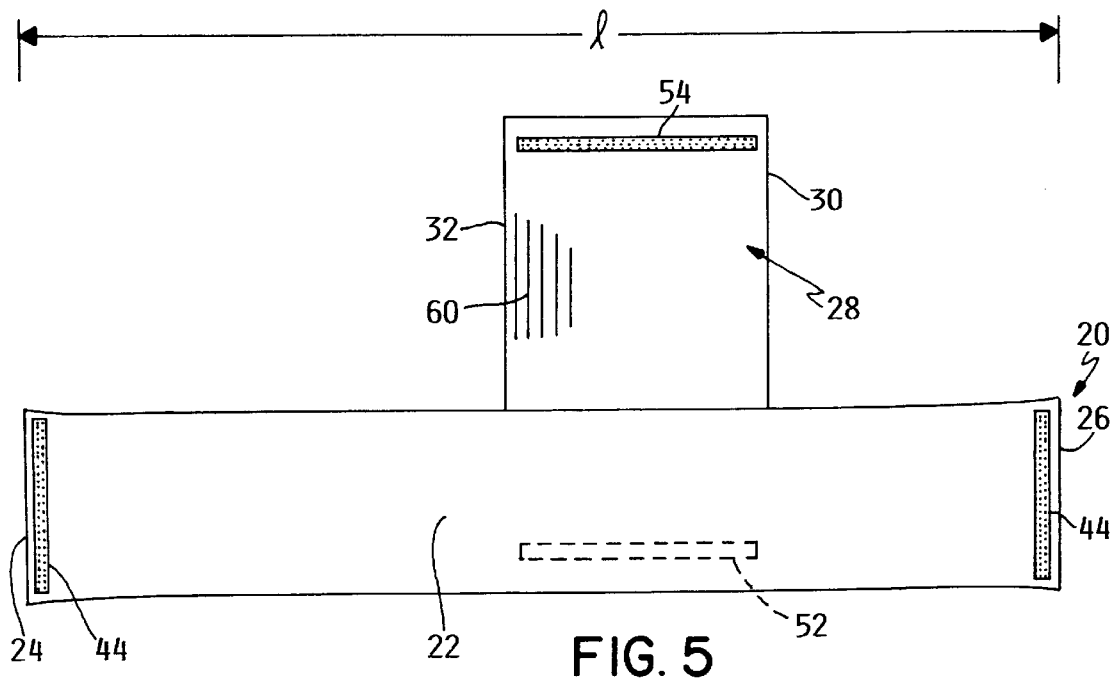
FIG. 5 is a plan view of the liner removed from the undershorts and further illustrating the first embodiment for fastening the crotch wrapping portion of the liner to the liner as illustrated in FIG. 4;.

This invention relates to a removable liner 20 for use with these undershorts for protecting undershorts 2 from staining. As shown in FIG. 5, liner 20 includes an elongated, generally rectangular body 22 that extends between a first end 24 and a second end 26. The length of body 22 between first and second ends 24 and 26, denoted as 1 in FIG. 5, is long enough to allow liner 20 to extend from back 6 of undershorts 2 at waistband 8 to front 4 of undershorts 2 at waistband 8. See FIG. 1.

When installed in undershorts 2, liner 20 droops or drapes downwardly to lie adjacent to and follow the curve of undershorts 2 from back 6 to front 4. In other words, liner 20 can be installed in undershorts 2 as shown in FIG. 1 and when so installed will cover the central portions of both back 6 and front 4 of undershorts 2. Liner 20 will lie adjacent to and on top of crotch 12 and immediately behind fly 14. Thus, liner 20 is effective to catch both urinary and fecal discharges.

FIGS. 1 and 2 show first end 24 of liner 20 attached to waistband 8 at the central portion of back 6 of undershorts 2. FIGS. 2 and 3 show second end 26 of liner 20 attached to waistband 8 at the central portion of front 4 of undershorts 2. As noted earlier, it is preferred that liner 20 have a length 1 that is long enough to allow liner 20 to extend over the entire length of undershorts 2 from waistband 8 at front 4 to waistband 8 at back 6 while following the curve of the undershorts in crotch 12. Doing so ensures that liner 20 will catch both fecal and urinary discharges. However, liner 20 could be shortened somewhat so that the first and second ends of liner 20 attach to back 6 and front 4 of undershorts 2 somewhat below waistband 8.

Liner 20 is provided with a sidewardly extending flap 28 located between the first and second ends 24 and 26 thereof as shown in FIG. 5. FIG. 5 illustrates liner 20 and flap 28 lying flat. Flap 28 is designed to wrap around at least a portion of crotch 12 of undershorts 2 when liner 20 is installed in undershorts 2. Accordingly, flap 28 will also be referred to as crotch wrapping flap 28 due to the function it performs. Crotch wrapping flap 28 is shown in FIG. 1 after installation and after flap 28 has been wrapped around a portion of crotch 12. When installed as shown in FIG. 1, crotch wrapping flap 28 is, for the most part, located outside of undershorts 2. However, that portion of body 22 of liner 20 from which flap 28 extends is still located interiorly of undershorts 2 overlying and lining at least a portion of crotch 12.

The purpose of crotch wrapping flap 28 is to securely attach liner 20 to undershorts 2 intermediate the first and second ends 24 and 26 of liner 20 and to protect the outside of crotch 12 from being stained by leakage around liner 20 in the crotch area of undershorts 2. The Applicant has found that crotch wrapping flap 28 helps keep liner 20 in place as well as serving to catch any leakage in this area of undershorts 2. Effectively, liner 20 is sealed to undershorts 2 by flap 28 in the area of crotch 12 so that leakage around the sides of liner 20 will not reach undershorts 2.

Crotch wrapping flap 28 is preferably approximately 6" to 10" long allowing flap 28 to have a top end 30 that is located on crotch 12 overlying a good deal of fly 14. The bottom end 32 of flap 28 will preferably reach into the lowermost, upwardly facing portion of crotch 12, though bottom end 32 could terminate at the very lower end of front 4 of undershorts 2 where crotch 12 begins to bend rearwardly to form its lowermost upwardly facing portion.

Liner 20 is removably attached to undershorts 2 using any convenient fastener 40. As shown herein, fastener 40 comprises a hook and pile fastener such as that known as Velcro. One portion 42 of the hook and pile fastener is located in a strip on the inside of waistband 8 at front 4 and back 6, while the other portion 44 of hook and pile fastener 40 is located in a strip on the first and second ends 24 and 26 of liner 20. Portion 42 could be the hook portion and portion 44 the pile portion or vise versa. In any event, first end 24 of liner 20 is removably secured to waistband 8 by pressing hook and pile fastener 40 together, i.e. by pressing fastener portions 42 and 44 together. See FIG. 2. Second end 26 of liner 20 is attached in the same way. See FIG. 3. Using hook and pile fasteners 40 allows liner 20 to be quickly and easily removed.

A similar hook and pile fastener 50 is used to secure crotch wrapping flap 28 to body 22 of liner 20 after flap 28 has been wrapped around crotch 12. In a first embodiment of fastener 50, as shown in FIGS. 4 and 5, one portion 52 of hook and pile fastener 50 is placed on the rear surface of body 22 of liner 20 in the area of body 22 that covers crotch 12 and the other portion 54 of hook and pile fastener 50 is placed on that surface of flap 28 that faces to the front after flap 28 has been wrapped around crotch 12. Thus, after flap 28 has been passed through one of leg holes 10, wrapped around crotch 12, and then passed back through the other leg hole 10 to overlie the opposite side of body 22, fastener 50 can be secured together by pressing flap 28 forwardly against liner body 22 as illustrated by the arrow A in FIG. 4 to secure flap 28 to liner 20.

An alternative placement of hook and pile fastener 50 for crotch wrapping flap 28 is shown in FIG. 4A. In this placement, the free edge of flap 28 is folded in front of liner 20 rather than passing around in back of liner 20. Hook and pile fastener portions 52 and 54 are now located on the front surface of liner body 22 and a rearwardly facing surface on the folded over edge of flap 28 as is illustrated in FIG. 4A. Flap 28 is now secured in place by pressing flap 28 rearwardly towards liner 20 as illustrated by the arrow B in FIG. 4A.

Figure 6:
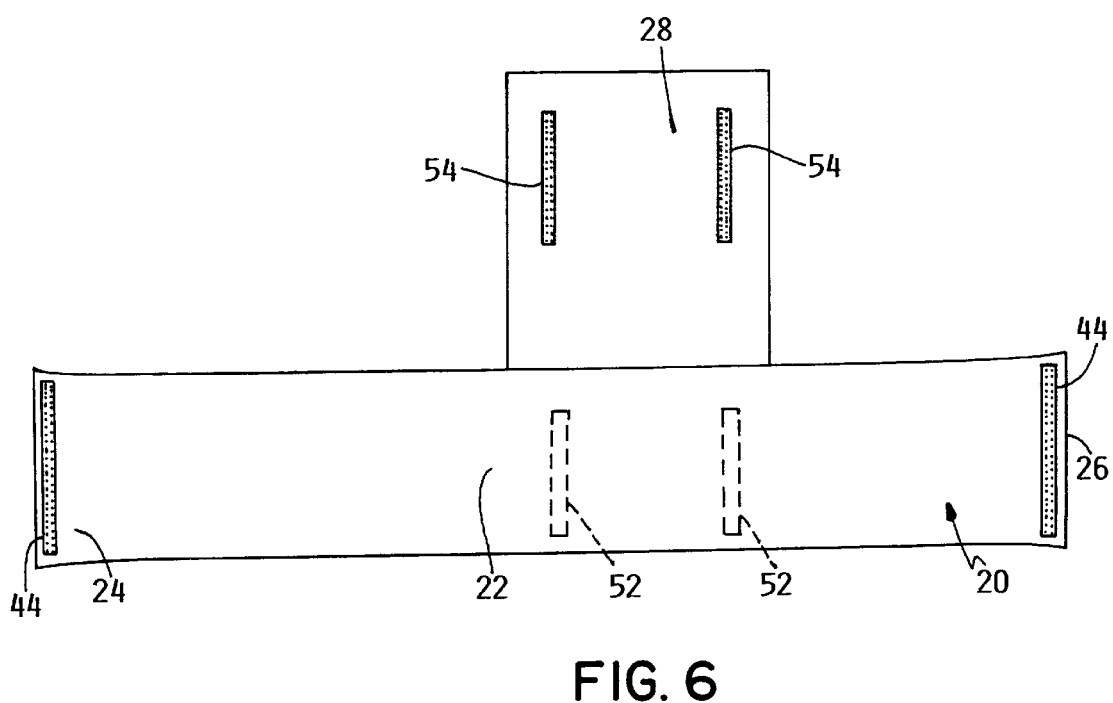
FIG. 6 is a plan view of the liner removed from the undershorts illustrating a third embodiment for fastening the crotch wrapping portion of the liner to the liner after the crotch wrapping portion has been wrapped around the crotch of the undershorts.

In the fastener 50 of FIGS. 4 and 4A, hook and pile fastener portions 52 and 54 run parallel to the length of liner 20 as shown in FIG. 5. Yet another embodiment as shown in FIG. 6 is to use a hook and pile fastener 50 in which the fastener potions 52 and 54 would run perpendicular to the length of liner 20 as is true of fasteners 40 on the first and second ends 24 and 26 of liner 20. For such a perpendicular fastener 50, two such fasteners 50 would be used, one at either end of flap 28. Accordingly, the exact orientation of fastener 50 used to fasten the free edge of flap 28 to liner 20 after flap 28 has wrapped around crotch 12 can vary.

Preferably, liner 20 is made from a suitable fabric material that can be washed and reused, such as cotton. As shown in the drawings, liner 20 can have a double thickness of material for increased absorption with the two thicknesses being labelled as a and b in FIGS. 2–4. However, a single thickness of material could also be provided. washing and reusing liner 20 is preferred from an environmental standpoint. In addition, because undershorts 2 themselves are already provided with half of the hook and pile fastener 40 needed to attach the first and second ends of liner 20 to undershorts 2, having a washable and reusable liner 20 makes use of the fact that the mating undershorts 2 are also washable and reusable. However, liner 20 could be made of a disposable material, such as an absorbent paper type material as is used in diapers, to be thrown away after a single use. For such a single use liner, chemically based, pressure sensitive adhesive strips would be preferably used in place of hook and pile fasteners 40 and/or 50.

The advantages provided by liners 20 of this invention should be apparent. They cover the entire length of undershorts 2 from waistband 8 at the front 4 of undershorts 2 to waistband 8 at the rear 6 of undershorts 2 passing behind front 4 of undershorts 2, over crotch 12 and then up in front of back 6 of undershorts 2. This provides maximum protection for both fecal and urinary discharges. In addition, crotch wrapping flap 28 ensures liner 20 will stay in place and lie adjacent the material of undershorts 2 along its entire length. Crotch wrapping flap 28 will also prevent leakage around crotch 12 and will serve to prevent any such leakage from seeping into contact with front 4 of undershorts 2. Accordingly, liner 20 of this invention serves to more fully and securely protect undershorts 2, and any outer garments worn over undershorts 2, from being soiled or stained.

Using a liner 20 as disclosed herein within a pair of undershorts 2 is advantageous in prevent undue soiling or staining of undershorts 2 or outer garments. Thus, undue cleaning of undershorts 2 or outer garments, or undue replacement of these items, is not required.

Figure 7:
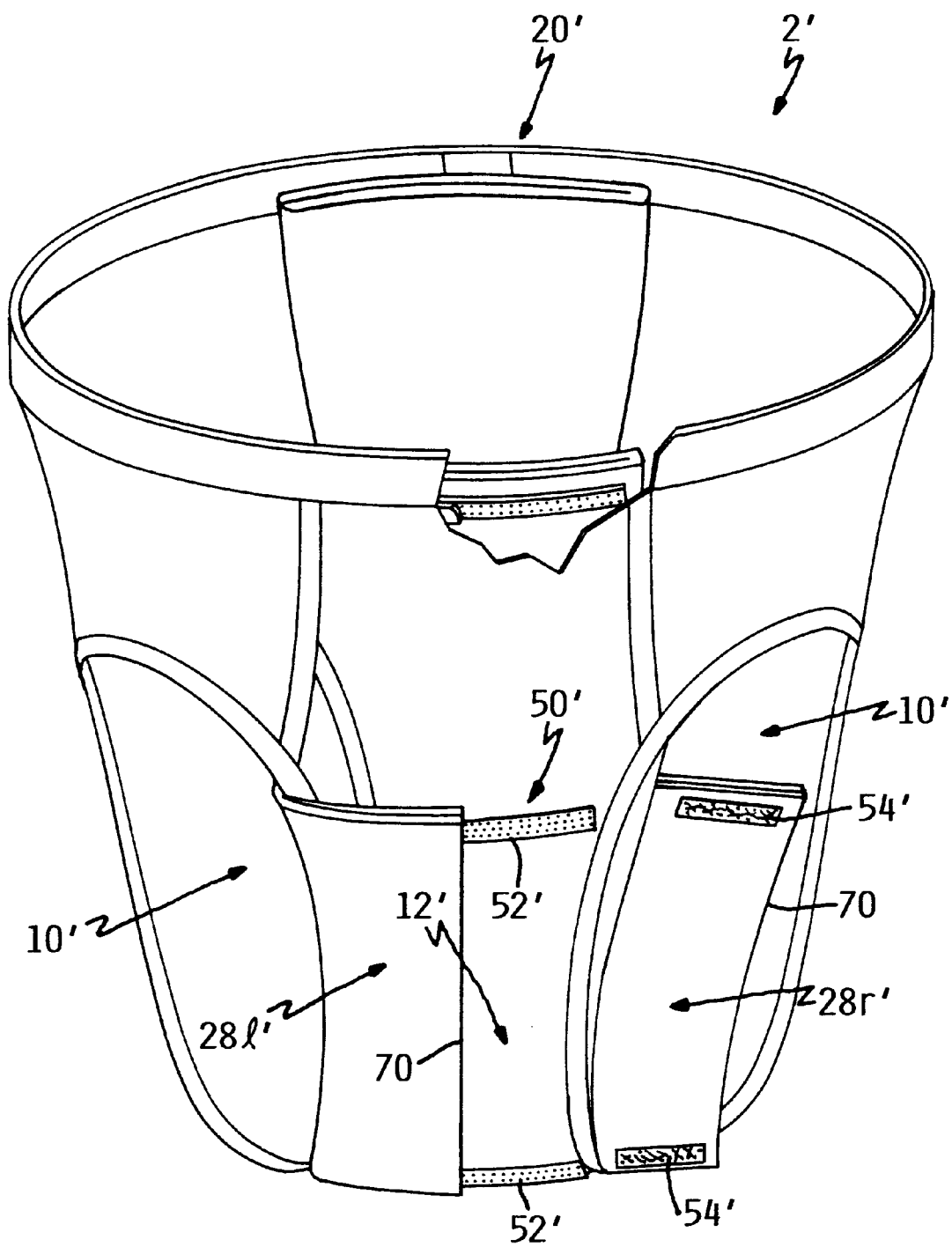
FIG. 7 is a perspective view of an alternative embodiment of a pair of undershorts according to this invention having a protective, removable liner.

FIG. 7 discloses an alternative embodiment for a pair of undershorts 2' according to this invention. In this embodiment, liner 20' is as shown in FIG. 1 except that liner 20' is now provided with two flaps 28l' and 28r' which stick out from opposite sides of liner 20' rather than just a single flap 28 which sticks out from one side of liner 20. Flap 28l' extends outwardly from the left side of liner 20' and flap 28r' extends outwardly from the right side of liner 20'. Each flap 28l' and 28r' is shorter than flap 28 with each flap 28l' and 28r' being intended to cover only about one half of crotch 12' of undershorts 2'.

The hook and pile fastener 50' is also changed in undershorts 2'. Hook and pile fastener portions 52' and 54' are now located on the front surface of crotch 12' and on those surfaces of flaps 28l' and 28r' which face or cover crotch 12' when flaps 28l' and 28r' are wrapped around their half of crotch 12'. Referring to FIG. 7, the left flap 28l' is illustrated adhered to crotch 12', but the right flap 28r' is shown before it has been pulled through the adjacent leg hole 10' and wrapped around its half of crotch 12' such that hook and pile fastener portions 52' and 54' are visible. Hook and pile fastener portions 52' and 54' are located in strips along the top and bottom edges of each flap 28l' and 28r' and at corresponding facing locations on the front of crotch 12'. As shown, the fastener portion 52' used on crotch 12 can be one long strip or band that can be engaged by both of the mating fastener portions 54' on the flaps 28l' and 28r', or could be split in the middle to comprise two separate fastener portions 52' which are side-by-side, one for each flap 28l' and 28r'.

In using undershorts 2' illustrated in FIG. 7, liner 20' is secured much as is liner 20 at waistband 8' at the front and back of the undershorts. When so installed, left flap 28l' will be positioned adjacent the left leg hole 10' and right flap 28r' will be positioned adjacent the right leg hole 10'. Each flap can be pulled through the adjacent leg hole and wrapped around the front of crotch 12' to cover approximately one half of crotch 12' due to the length of the flap. The mating hook and pile fasteners 52' and 54' can be secured simply by pressing each flap 28l' or 28r' rearwardly against the front of crotch 12'. The Applicant has found that this type of fastening system is easier to secure than some of the fasteners 50 shown in FIGS. 1–6, though it does require that fastener portions 52' be affixed to the front of crotch 12'.

Left and right flaps 28l' and 28r' are designed to each cover about one half of crotch 12' such that their free edges or ends 70 will be adjacent one another when both flaps are secured to the front of crotch 12'. However, each flap 28l' and 28r' could be shorter than this such that a gap is present between the two when they are secured to crotch 12' as long as each flap 28l' and 28r' is long enough to wrap around the edge of the adjacent leg hole 10' and extend at least partially onto the front of crotch 12' to thereby seal the edge of the leg hole 10' and protect against leakage between the liner 20' and the leg hole 10'.

Various modifications of this invention will be apparent to those skilled in the art. For example, the fasteners 50' shown in FIG. 7 which secure the flap to the outside or front of crotch 12' could be used even with a single flap extending all or most of the way across the front of crotch 12', or could be used in addition to fasteners 50 shown in FIGS. 1–6 to better secure any of liners 20 shown in FIGS. 1–6 to the undershorts. In addition, the material used in liner 20 could have various forms, including the use of a ribbed fabric to form flap 28 with the ribs running transversely across flap 28. A few such ribs 60 are shown in FIG. 5. Such ribs 60 can help contract flap 28 slightly to ensure that it tightly wraps around crotch 12. Accordingly, this invention is to be limited only by the appended claims.

I claim:

1. A pair of undershorts having a liner, which comprises:
   (a) a pair of undershorts which includes a front, a back, a waistband, two leg holes, and a crotch between the leg holes; and
   (b) a liner attached to the undershorts and covering at least a portion of the front and a portion of the back of the undershorts, the liner having at least one sidewardly extending flap that is positioned to extend out through one leg hole and wrap around at least a portion of the crotch, wherein the flap is long enough to wrap completely around the portion of the crotch and to pass back through the other leg hole, and wherein the flap is detachably secured to the liner after the flap has been wrapped around the portion of the crotch.

2. The undershorts of claim 1, wherein the flap is detachably secured to the liner by at least one hook and pile fastener.

3. The undershorts of claim 2, wherein the hook and pile fastener has two mating portions, wherein the flap is wrapped around such that a free edge of the flap lies in back of the liner, wherein one portion of the hook and pile fastener is on a rear face of the liner and the other portion of the hook and pile fastener is on a forwardly facing surface of the flap after the flap has been wrapped around the portion of the crotch, the hook and pile fastener portions being pressed together by pressing the flap forwardly into contact with the liner.

4. The undershorts of claim 2, wherein the hook and pile fastener has two mating portions, wherein the flap is wrapped around such that a free edge of the flap lies in front of the liner, wherein one portion of the hook and pile fastener is on a front face of the liner in the crotch and the other portion of the hook and pile fastener is on a rearwardly facing surface of the flap after the flap has been wrapped around the crotch, the hook and pile fastener portions being pressed together by pressing the flap rearwardly into contact with the liner.

5. The undershorts of claim 1, wherein the liner is provided with two flaps extending outwardly from opposite sides of the liner, wherein each flap is long enough to pass out through an adjacent leg hole and to wrap partially around the portion of the crotch, and wherein each flap is detachably secured to the portion of the crotch after each flap has been partially wrapped around the portion of the crotch.

6. The undershorts of claim 5, wherein each flap is detachably secured to the portion of the crotch by at least one hook and pile fastener.

7. The undershorts of claim 6, wherein the hook and pile fastener has two mating portions, wherein one portion of the hook and pile fastener is on a front face of the portion of the crotch and the other portion of the hook and pile fastener is on a rearwardly facing surface of each flap after the flap has been partially wrapped around the portion of the crotch, the hook and pile fastener portions being pressed together by pressing the flaps rearwardly into contact with the front face of the portion of the crotch.

8. The undershorts of claim 6, wherein a hook and pile fastener is used along both top and bottom edges of each flap.

9. The undershorts of claim 1, wherein the liner is detachably secured to the undershorts.

10. The undershorts of claim 1, wherein the liner has opposed first and second ends, and wherein the liner is detachably secured to the undershorts at its first and second ends.

11. The undershorts of claim 10, wherein the liner is detachably secured to the undershorts at its first and second ends by hook and pile fasteners.

12. The undershorts of claim 1, wherein the liner has opposed first and second ends, wherein the first end of the liner extends up to the waistband of the undershorts at the back of the undershorts and the second end of the liner extends up to the waistband of the undershorts at the front of the undershorts to cover substantially the entire front and back of the undershorts.

13. The undershorts of claim 12, wherein the first and second ends of the liner are attached to the waistband by detachable fasteners.

14. A pair of undershorts having a liner, which comprises:
(a) a pair of undershorts which includes a front, a back, a waistband, two leg holes, and a crotch between the leg holes; and
(b) a liner attached to the undershorts and covering substantially the entire front and back of the undershorts, the liner having a first end attached to the undershorts at the front adjacent the waistband and a second end attached to the undershorts at the back adjacent the waistband, the liner extending between its first and second ends with a length and width which is sufficient to drape downwardly between the first and second ends of the liner to closely cover and overlie both the back, the front and the crotch of the undershorts.

15. The undershorts of claim 14, wherein the liner is generally rectangular between its first and second ends.

16. The undershorts of claim 15, wherein the liner includes at least one sidewardly extending flap that is positioned between its first and second ends to extend out through one leg hole and wrap around at least a portion of the crotch.

17. The undershorts of claim 16, wherein the flap has transversely extending ribs in its material.

18. The undershorts of claim 15, wherein the first and second ends of the liner are detachably secured to the undershorts.

19. A liner for a pair of men's undershorts of the type which includes a front, a back, a waistband, two leg holes, and a crotch between the leg holes, the front of the undershorts having a fly on a portion of the crotch which fly includes an opening for urination, the liner comprising:
(a) an elongated body extending between opposed first and second ends thereof; and
(b) at least one flap secured along one side of the flap to one longitudinal edge of the body between the first and second ends of the body with the flap extending to the side away from the body to terminate in a free end, the flap being positioned on the body to extend out through one leg hole and having a length which is sufficient to wrap around at least a portion of the crotch when the first and second ends of the body are secured to the front and back of the undershorts, the flap further being positioned on the body to wrap around the portion of the crotch which carries the fly such that the flap is positioned substantially on the front of the undershorts.

20. The liner of claim 19, wherein the body is provided with two flaps extending outwardly from opposite sides of the body, wherein each flap is long enough to pass out through an adjacent leg hole and to wrap partially around the portion of the crotch, and wherein each flap is detachably secured to the portion of the crotch after each flap has been partially wrapped around the portion of the crotch.

* * * * *